United States Patent
Kim et al.

(10) Patent No.: US 11,607,378 B2
(45) Date of Patent: Mar. 21, 2023

(54) COSMETIC COMPOSITION COMPRISING AMIDE-BASED COMPOUND

(71) Applicant: Neopharm Co., Ltd., Daejeon (KR)

(72) Inventors: Yoon Kim, Daejeon (KR); Kyung Sook Yoo, Daejeon (KR); Bu-Mahn Park, Daejeon (KR); Yu Ra Jung, Daejeon (KR); Hye Seong Shin, Daejeon (KR)

(73) Assignee: Neopharm Co., Ltd., Daejeon (KR)

( * ) Notice: Subject to any disclaimer, the term of this patent is extended or adjusted under 35 U.S.C. 154(b) by 239 days.

(21) Appl. No.: 17/198,703

(22) Filed: Mar. 11, 2021

(65) Prior Publication Data

US 2021/0283031 A1    Sep. 16, 2021

(30) Foreign Application Priority Data

Mar. 13, 2020  (KR) .......... 10-2020-0031133

(51) Int. Cl.
| | | |
|---|---|---|
| *A61K 8/42* | (2006.01) | |
| *A61K 8/02* | (2006.01) | |
| *A61Q 17/04* | (2006.01) | |
| *A61Q 19/00* | (2006.01) | |
| *A61Q 19/10* | (2006.01) | |

(52) U.S. Cl.
CPC .............. *A61K 8/42* (2013.01); *A61K 8/0208* (2013.01); *A61Q 17/04* (2013.01); *A61Q 19/007* (2013.01); *A61Q 19/10* (2013.01); *A61K 2800/5922* (2013.01)

(58) Field of Classification Search
None
See application file for complete search history.

(56) References Cited

U.S. PATENT DOCUMENTS

2002/0187915 A1* 12/2002 Sakai .................... C11D 1/652
510/427

* cited by examiner

*Primary Examiner* — Nannette Holloman
(74) *Attorney, Agent, or Firm* — Blank Rome LLP

(57) ABSTRACT

Provided is a cosmetic composition for protection of the skin against reactive oxygen species, ultraviolet rays, or blue light, which includes an amide-based compound. The cosmetic composition according to the present invention can effectively inhibit cell damage caused by the reactive oxygen species, the ultraviolet rays, or the blue light and protect the skin without irritating the skin, and can simultaneously aid in recovering the damaged skin.

10 Claims, 2 Drawing Sheets

COSMETIC COMPOSITION COMPRISING AMIDE-BASED COMPOUND

CROSS-REFERENCE TO RELATED APPLICATIONS

This application claims priority under 35 U.S.C. § 119 to Korean Patent Application No. 10-2020-0031133, filed on Mar. 13, 2020, in the Korean Intellectual Property Office, the disclosure of which is incorporated herein by reference in its entirety.

TECHNICAL FIELD

The following disclosure relates to a cosmetic composition including an amide-based compound, and more particularly, to a cosmetic composition for protection of the skin against reactive oxygen species, ultraviolet rays, or blue light, which includes an amide-based compound.

BACKGROUND

Ultraviolet rays have wavelengths that are radiated from the rays of the sun, and thus mainly cause erythema, edema, freckles, skin cancer, or the like in the skin. In general, the ultraviolet rays are divided into ultraviolet ray A (320 to 400 nm), ultraviolet ray B (280 to 320 nm), and ultraviolet ray C (240 to 280 nm) according to the order of wavelengths. The ultraviolet ray A is characterized by having long wavelengths and low energy, and is known to penetrate the dermis of the skin to induce skin cancer and wrinkles, promote melanogenesis, and the like, thereby causing skin damage and cell stimulation. However, the ultraviolet ray A has a poor energy intensity. The ultraviolet ray B is characterized by having short wavelengths and high energy, has the most influence on the human body in a photobiological aspect among the ultraviolet rays, and mainly causes photodamage to the skin. The ultraviolet ray B penetrates the epidermis of the skin to cause erythema, freckles, edema, and the like because it has a high energy intensity. Also, when the skin is chronically exposed to the ultraviolet ray B, the ultraviolet ray B has consequences such as skin damage, immunosuppression, skin cancer, and apoptosis. The ultraviolet ray C is lost without reaching the surface of the earth while passing through the ozone layer.

In recent years, the development of cosmetic compositions using a sunblock, which blocks penetration of ultraviolet rays to protect cells, or components, which have a function of inhibiting generation of reactive oxygen species in the cells by ultraviolet rays, has been actively carried out in order to suppress skin damage by such ultraviolet rays.

SUMMARY

An embodiment of the present invention is directed to providing a cosmetic composition for protection of the skin against reactive oxygen species, ultraviolet rays, or blue light.

Another embodiment of the present invention is directed to providing a cosmetic composition capable of protecting the skin by effectively inhibiting generation of reactive oxygen species generated by ultraviolet rays or blue light or removing the reactive oxygen species.

In a general aspect, a cosmetic composition for protection of the skin against reactive oxygen species, ultraviolet rays, or blue light includes N-(2-hydroxyethyl)-2-methyl-hexanamide, N-(2-ethyl-1-oxohexyl)glycine methyl ester, or a combination thereof as an active ingredient.

The cosmetic composition according to one embodiment of the present invention may inhibit generation of reactive oxygen species or remove the reactive oxygen species.

The cosmetic composition according to one embodiment of the present invention may inhibit generation of reactive oxygen species selected from hydrogen peroxide, a superoxide anion, a hydroxy radical, and the like, or may remove the reactive oxygen species.

The cosmetic composition according to one embodiment of the present invention may inhibit generation of reactive oxygen species generated by ultraviolet rays or blue light or remove the reactive oxygen species to exhibit a skin protection activity.

The cosmetic composition according to one embodiment of the present invention may increase an activity of SOD to exhibit a skin protection activity.

The cosmetic composition according to one embodiment of the present invention may decrease expression of p16 to exhibit a skin protection activity.

In the cosmetic composition according to one embodiment of the present invention, the active ingredient may be included at 0.001 to 5% by weight, based on the total weight of the cosmetic composition.

The cosmetic composition according to one embodiment of the present invention may be formulated into a lotion, a toner, a face lotion, an eye cream, a nourishing cream, a massage cream, a cleansing cream, a cleansing foam, a cleansing water, an essence, a pack, or the like.

In another general aspect, a method for improving skin conditions using, as a cosmetic material, a composition including N-(2-hydroxyethyl)-2-methyl-hexanamide, N-(2-ethyl-1-oxohexyl)glycine methyl ester, or a combination thereof as an active ingredient.

In the method according to one embodiment of the present invention, the improvement may be achieved by inhibiting generation of reactive oxygen species and removing the reactive oxygen species; increasing an activity of SOD; and decreasing expression of P16.

DETAILED DESCRIPTION OF EMBODIMENTS

Figure 1:
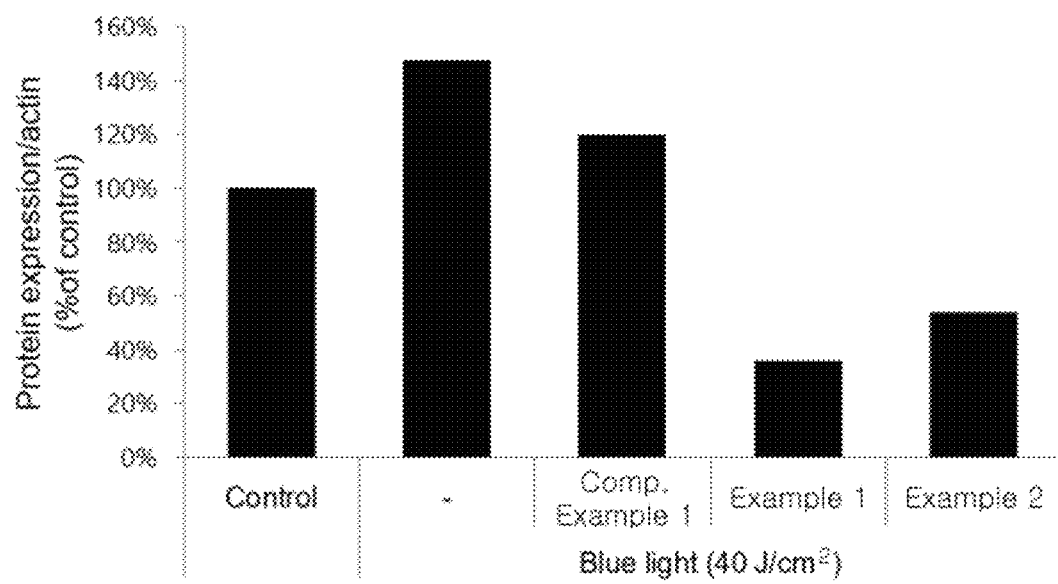
FIG. 1 is a diagram showing an expression level of $p16^{INK4A}$ in cells damaged by blue light, as observed by Western blot analysis.

A cosmetic composition including an amide-based compound according to the present invention will be described in detail. In this case, unless otherwise defined, the technical and scientific terms used herein have the same meaning as commonly understood by one of ordinary skill in the art to which the present invention pertains. In the following description, a description of known functions and configurations, which may unnecessarily obscure the subject matter of the present invention, will be omitted.

The term "reactive oxygen species (ROS)" used in this specification refers to oxygen that is in an unstable state. In this case, oxygen is overproduced due to environmental pollution, chemicals, ultraviolet rays, blood circulatory disturbance, stress, and the like. The reactive oxygen species cause an action of oxidation in the human body. For example, the reactive oxygen species may cause damage to cell membranes, DNA, and all other cellular structures, and may lose or deteriorate their functions according to a range of damage. Also, the reactive oxygen species causes oxidative stress in the skin cells.

The term "ultraviolet rays" used in this specification are divided into ultraviolet ray A (320 to 400 nm), ultraviolet ray B (280 to 320 nm) and ultraviolet ray C (240 to 280 nm) according to the order of wavelengths. Among them, the mid-wavelength ultraviolet ray (UVB) refers to a source of light that causes direct damage to the skin cells and also causes indirect damage by generation of the reactive oxygen species. The generation of the reactive oxygen species is regulated by an antioxidant defense system. However, when an excessive amount of the reactive oxygen species are produced by pollution, solar ultraviolet rays, chemical oxidants, microorganisms, and the like, such a defense system collapses. As a result, the reactive oxygen species cause oxidative damage to DNAs, lipids, proteins in the cells and provoke oxidative stress by ultraviolet rays, the reactive oxygen species may also cause inflammation and cell necrosis in the skin.

The term "blue light" used in this specification refers to a source of light having a wavelength between 380 nm and 500 nm. In particular, the blue light known to emit from electronic devices such as LED lamps, smart phones, computers, and the like has energy higher than visible rays having other wavelengths, and causes adverse influence on the skin because the skin is frequently exposed to blue light in daily life.

The present inventors have repeatedly conducted research on cosmetic materials, and found that an amide-based compound having a certain structure exerts a significant effect in removing reactive oxygen species induced from ultraviolet rays or blue light as well as reactive oxygen species induced from hydrogen peroxide, and the like, and simultaneously exerts an excellent effect in increasing the SOD activity. Also, the present inventors have found that compounds having similar structural characteristics also exhibit a non-specific effect, and further conducted the research.

In particular, the present inventors have focused on N-(2-hydroxyethyl)-2-methyl-hexanamide and N-(2-ethyl-1-oxohexyl)glycine methyl ester. The aforementioned amide-based compounds have a significant effect of removing the reactive oxygen species as well as a significant effect of increasing the SOD activity reduced by the reactive oxygen species. Also, it was confirmed that an effective amount of the amide-based compounds having an effect of removing the reactive oxygen species has no cytotoxicity in an experiment using a human dermal fibroblast cell line. Accordingly, based on such effects, the present inventors have found a use of the amide-based compounds, which has not been known in the prior art, and a surprisingly remarkably improved effect in their use, and thus proposed the present invention.

Hereinafter, the present invention will be described in detail.

A cosmetic composition of the present invention includes N-(2-hydroxyethyl)-2-methyl-hexanamide, N-(2-ethyl-1-oxohexyl)glycine methyl ester, or a combination thereof as an active ingredient, and thus specific functions thereof are as follows.

The cosmetic composition of the present invention may be a cosmetic composition for protection of the skin against reactive oxygen species, ultraviolet rays, or blue light. Also, the reactive oxygen species are not limited as long as they are overproduced oxygen species that cause oxidative stress to the skin. However, the reactive oxygen species may be, for example, selected from hydrogen peroxide, a superoxide anion, a hydroxy radical, and the like.

Specifically, the cosmetic composition of the present invention may achieve i) an effect of removing reactive oxygen species induced from blue light, ii) an effect of inhibiting generation of the reactive oxygen species, iii) an effect of increasing an activity of SOD, and iv) an effect of inhibiting expression of p16, and thus may protect the skin, and may also improve the collapse of homeostasis of the skin.

Also, the cosmetic composition of the present invention protects cells from the reactive oxygen species induced from ultraviolet rays or blue light, and also inhibits an apoptotic body to protect cells from apoptosis.

The cosmetic composition of the present invention exhibits an effect of protecting the skin against reactive oxygen species, ultraviolet rays, or blue light, and also exhibits a significant effect in improving the damaged skin cells induced therefrom due to the simultaneous achievement of the effects as described above. Therefore, the cosmetic composition of the present invention may be effectively used for skin regeneration.

Also, the present invention may be used by a method of applying the aforementioned cosmetic composition of the present invention to the skin to improve skin conditions. The improvement may be achieved by inhibiting generation of reactive oxygen species and removing the reactive oxygen species; increasing an activity of SOD; and effectively suppressing expression of P16.

As described above, the cosmetic composition of the present invention is characterized by including, as an active ingredient, an amide-based compound selected from N-(2-hydroxyethyl)-2-methyl-hexanamide, N-(2-ethyl-1-oxohexyl)glycine methyl ester, and a combination thereof, and the amide-based compound has the following structure.

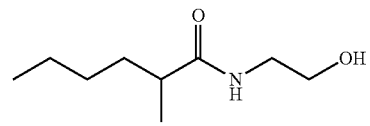

N-(2-hydroxyethyl)-2-methyl-hexanamide

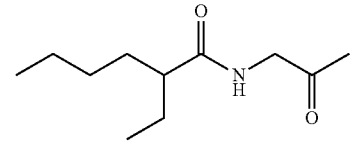

N-(2-ethyl-1-oxohexyl)glycine methyl ester

As one example, the cosmetic composition of the present invention may also include a pharmaceutically acceptable salt of the amide-based compound or a solvate and stereoisomer thereof as the active ingredient according to one aspect of the present invention.

The cosmetic composition of the present invention effectively inhibits generation of reactive oxygen species or removes the reactive oxygen species to exhibit a skin protection activity.

The cosmetic composition of the present invention may increase an activity of SOD reduced by the reactive oxygen species, the ultraviolet rays, or the blue light.

Also, the cosmetic composition of the present invention protects the skin by inhibiting expression of p16. The p16 is a gene associated with the cell growth, and may be effective in improving skin conditions when its expression level is suppressed. Here, the cosmetic composition of the present invention is involved in the inhibition of expression of the gene.

In addition, the amide-based compound may be used safely because the amide-based compound does not cause cytotoxicity and cell stimulation when used in an amount that exerts a significant effect on the skin. Also, the amide-based compound may stably maintain its effect in a formulation, and does not cause a phenomenon in which it is not precipitated or separated in the formulation, and also has good storage stability as well.

In the cosmetic composition according to one embodiment of the present invention, the active ingredient may be included at 0.001 to 5% by weight, based on the total weight of the cosmetic composition. Specifically, the active ingredient may be included at 0.001 to 3% by weight, and more specifically 0.01 to 1% by weight. When the active ingredient is included in this range, the cosmetic composition of the present invention has an effect (i.e., a significant use) required in the present invention without impairing the stability of the formulation, which is more preferable.

Also, in the cosmetic composition according to one embodiment of the present invention, when the active ingredient is included as one aspect of a mixture, the active ingredient may give a more significant synergy, which is preferable. In particular, when the combination of N-(2-hydroxyethyl)-2-methyl-hexanamide and N-(2-ethyl-1-oxohexyl)glycine methyl ester is included as the active ingredient, the combination exhibits more significance in an effect of removing the reactive oxygen species.

As one example, when the mixed active ingredients (at a weight ratio of 1:1) are included, the mixed active ingredients exhibit a synergistic effect, compared to when the same amount of the single ingredient used is included.

As one example, in the case of the mixed active ingredients, the N-(2-hydroxyethyl)-2-methyl-hexanamide and the N-(2-ethyl-1-oxohexyl)glycine methyl ester may be mixed at a weight ratio of 0.01:99.99 to 99.99:0.01, and may be specifically mixed at a weight ratio of 1:9 to 9:1, and more specifically a weight ratio of 1:1 to 9:1, but the present invention is not limited thereto.

The cosmetic composition according to one embodiment of the present invention may include the aforementioned active ingredient and the balance of water. In this case, it is true that the cosmetic composition according to one embodiment of the present invention may be formulated into various aspects.

The cosmetic composition according to one embodiment of the present invention may be formulated into general emulsion formulations, solubilization formulations, and the like using a preparation method commonly known in the art.

As one example, the cosmetic composition may be formulated into a formulation selected from a lotion, a toner, a face lotion, an eye cream, a nourishing cream, a massage cream, a cleansing cream, a cleansing foam, a cleansing water, an essence, a pack, and the like, but the present invention is not limited thereto.

Also, the cosmetic composition may further properly include an additional additive according to a purpose. In addition to the amide-based compound, the cosmetic composition may further include a component selected from an anti-wrinkle component, an antioxidant component, a whitening component, and the like, all of which are known in the art. As one example, the additional additive may be selected from retinoic acid, TGF, an animal placenta-derived protein, betulinic acid, a chlorella extract, and the like, but the present invention is not limited thereto.

In addition, the cosmetic composition may further include one or more additives selected from one or more aqueous additives selected from a stabilizing agent, an emulsifying agent, a thickening agent, a moisturizing agent, a liquid crystal film-enhancing agent, a pH regulating agent, an antibacterial agent, a water-soluble polymer, a film-forming agent, a metal ion-sequestering agent, an amino acid, an organic amine, a polymer emulsion, a pH adjusting agent, a skin nutrient, an antioxidant, an antioxidative aid, a preservative, a fragrance, and the like; and one or more oily additives selected from fat and oils, waxes, a hydrocarbon oil, a higher fatty acid oil, a higher alcohol, a synthetic ester oil, a silicone oil, and the like.

In this case, each of the additives may be included at 0.001 to 20% by weight, and may be specifically included at 0.01 to 10% by weight, and more specifically 0.05 to 5% by weight, based on the total weight of the cosmetic composition, but the present invention is not limited thereto.

(Evaluation Method)

1. Analysis of Expression Level of $p16^{INK4A}$ (1) An expression level of $p16^{INK4A}$ was determined through Western blot in Examples and Comparative Examples of the present invention.

Specifically, human dermal fibroblasts were cultured in a 12-well plate containing a Dulbecco's modified eagle medium (DMEM) medium supplemented with 10% fetal bovine serum (FBS) to attach $1.5 \times 10^5$ (1 mL/well) human dermal fibroblasts to the 12-well plate. The human dermal fibroblasts were cultured for 24 hours, and the medium was replaced with a 1% fetal bovine serum medium. Then, the human dermal fibroblasts were exposed to blue light of 40 $J/cm^2$, and then treated with each of the samples (100 μM) of Examples and Comparative Examples. Thereafter, the cells were additionally cultured at 37° C. for 24 hours. Then, the cells were recovered, and each of these samples was subjected to Western blot to analyze an expression level of $p16^{INK4A}$ in the dermal fibroblasts. Each of samples of Examples 1 and 2 and Comparative Example 1 including the amide-based compound having a structure shown in the following Table 1 was used as the sample.

The results thus obtained are shown in FIG. 1 below. The control of FIG. 1 represents an experimental group in which the cells were not treated with the sample, and (-) represents a result of the experimental group exposed to blue light.

2. Confirmation of Effect of Removing Reactive Oxygen Species (ROS)

An effect of removing the reactive oxygen species was determined for the samples of Examples and Comparative Examples of the present invention.

An image analysis for generation of reactive oxygen species (ROS) in the cells was carried out by seeding $1 \times 10^5$ (100 μL/well) dermal fibroblasts in a 12-well plate to which a cover slip was attached. The dermal fibroblasts were exposed to blue light of 40 $J/cm^2$, and then treated with each of the samples (100 μM) of Examples and Comparative Examples. Then, the cells were additionally cultured at 37° C. for 24 hours.

After 24 hours, 100 μM DCF-DA was put into each well, and the cells were cultured at 37° C. for 45 minutes. After the cells were washed with PBS, the stained cells were put on a microscope slide containing a mounting medium. A microscopic image was observed as a fluorescent microscopic image.

Figure 2:
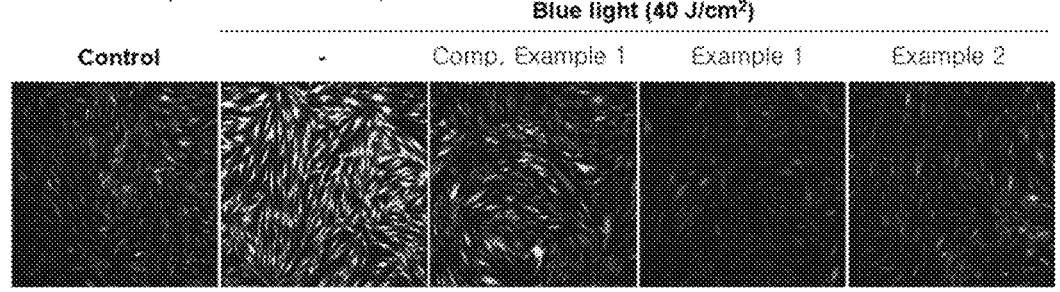
FIG. 2 is an image showing a change in activity of reactive oxygen species after treatment with blue light.
Figure 2:
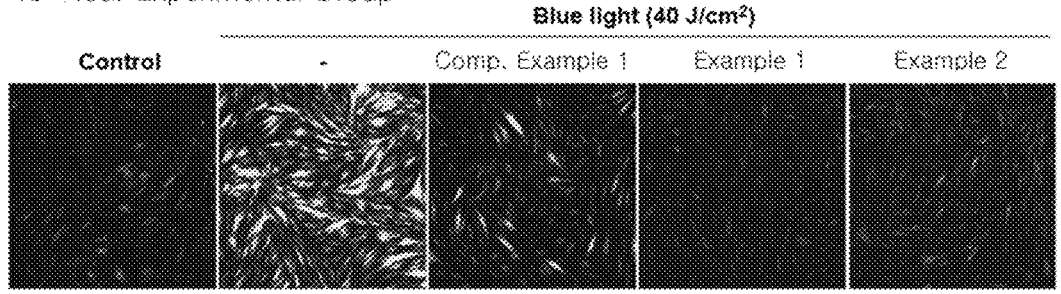

The results thus obtained are shown in FIG. 2 below.

3. Confirmation of Effect on Antioxidant Activity

Effects of the samples of Examples and Comparative Examples of the present invention on a change in antioxidant activity after irradiation with blue light were confirmed.

Specifically, $1.5 \times 10^5$ (1 mL/well) dermal fibroblasts were seeded in a 6-well plate, and cultured for 24 hours. The dermal fibroblasts were exposed to blue light of 40 J/cm$^2$, and then treated with each of the samples (100 μM) of Examples and Comparative Examples. After 48 hours, the cells were recovered. The cells were dissolved in a cell lysis buffer (pH 7.4) containing 0.1 M Tris/HCl, 0.5% Triton X-100, 5 mM β-ME, and 0.1 mg/ml PMSF, and a supernatant separated by centrifugation was then analyzed using a Superoxide Dismutase Activity Assay kit (ab65354). Then, the absorbance was measured at a wavelength of 450 nm in a microplate reader.

Figure 3:
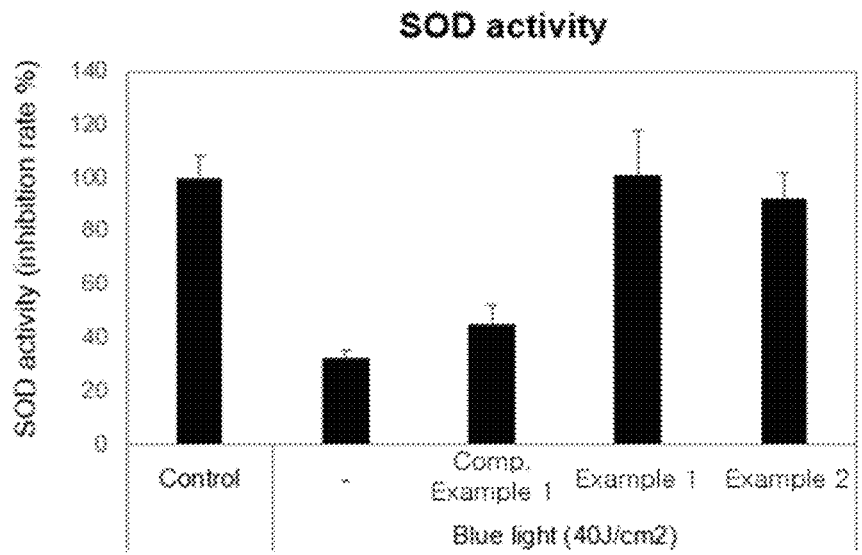
FIG. 3 is a diagram showing a change in activity of an antioxidant enzyme after treatment with blue light.

The results thus obtained are shown in FIG. 3 below.

4. Confirmation of Effect on Generation of Carbonylated Protein

An artificial skin (EpiDermFT™ from MatTek, Ashland, USA) was purchased, and then stabilized for 18 hours in an exclusive medium (EFT-400). 50 μL of each of the samples of Examples and Comparative Examples was applied to the artificial skin at a concentration of 0.3%, and then cultured for an hour. The artificial skin was exposed to blue light of 40 J/cm$^2$. After 48 hours, the artificial skin tissue was fixed in 10% formaldehyde, and embedded into paraffin. Thereafter, the tissue was microtomed into sections with a size of 5 pam. Then, the microtomed tissue was used to confirm an effect on a change in activity of the carbonylated protein.

The tissue was stained by a DNPH assay using an immunocytochemical (ICC) staining method, and then observed in a fluorescent microscopic image. Thereafter, the microscopic image was digitized using an image J program.

Figure 4:
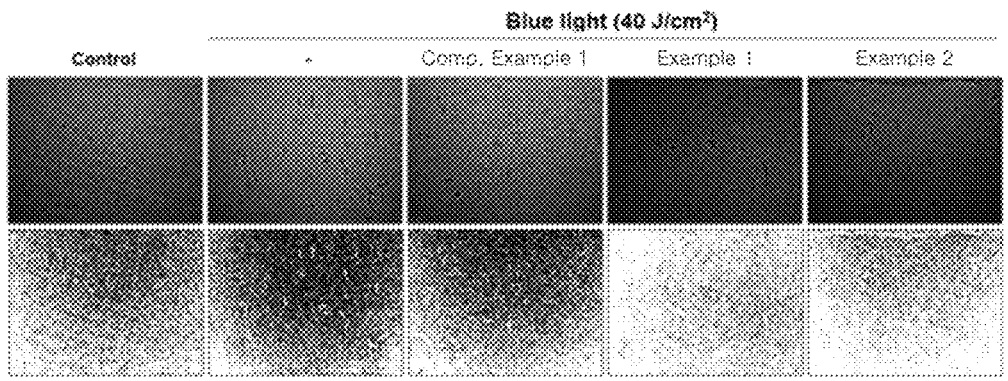
FIG. 4 is an image showing a change in activity of a carbonylated protein by means of a DNPH assay using an ICC staining method after an artificial skin is treated with blue light, and is a graph showing the results of quantitatively analyzing the change in activity.
Figure 4:
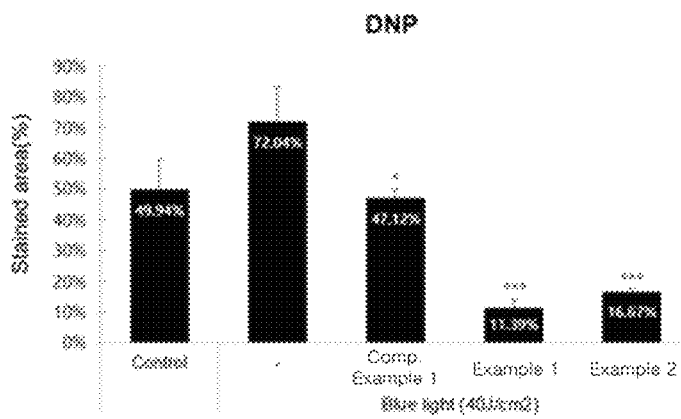

The results thus obtained are shown in FIG. 4 below.

Examples 1 and 2

The evaluation method was performed using the amide-based compounds having a structure shown in the following Table 1. The sample used as an experimental group in each of the Examples was prepared at various concentrations according to each evaluation method.

Comparative Examples 1 and 2

The evaluation method was performed using the amide-based compounds having a structure shown in the following Table 1. The sample of each of Comparative Examples was also prepared at various concentrations according to each evaluation method.

TABLE 1

Example 1

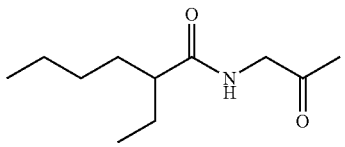

TABLE 1-continued

Example 2

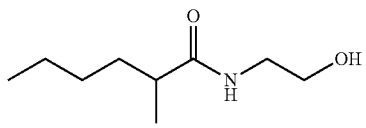

Comparative Example 1

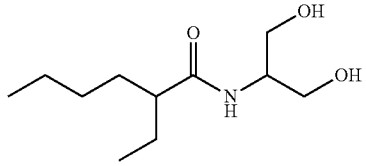

Comparative Example 2

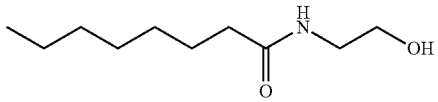

Example 1 N-(2-ethyl-1-oxohexyl)glycine methyl ester
Example 2: N-(2-hydroxyethyl)-2-methyl-hexanamide
Comparative Example 1: N-(1,3-dihydroxy propan-2-yl)-2-ethylhexanamide
Comparative Example 2: N-(2-hydroxyethyl)octanamide As shown in FIG. 1 below, an expression level of p16$^{INK4A}$ was determined by Western blot analysis after treatment with blue light. It was confirmed that the expression of p16$^{INK4A}$ increased in the experimental group treated with blue light of 40 J/cm$^2$, indicating that the cell damage was induced by blue light in the human dermal fibroblasts. To check whether the expression of p16$^{INK4A}$ increased by the irradiation with blue light was regulated by the compounds (Examples 1 and 2) of the present invention, it was also confirmed that the expression of p16$^{INK4A}$ was significantly reduced by the samples treated with the compounds (Examples 1 and 2) of the present invention after the artificial skin was irradiated with blue light at the same conditions. Specifically, it was confirmed that an effect of decreasing the expression of p16$^{INK4A}$ by the samples treated with the compounds (Examples 1 and 2) of the present invention corresponded to levels of 35.9% and 53.9%, compared to 120% of Comparative Example 1. This corresponds to a significant difference in the expression level of p16$^{INK4A}$.

As shown in FIG. 2 below, it was revealed that all the samples treated with the compounds of the present invention were excellent in significantly reducing the generation of the reactive oxygen species and removing the generated reactive oxygen species. On the other hand, the sample of Comparative Example 1 did not exhibit a significant effect in inhibiting the generation of the reactive oxygen species and removing the generated reactive oxygen species as well.

As shown in FIG. 3 below, it was confirmed that the samples treated with the compounds (Examples 1 and 2) of the present invention had an excellent effect of increasing the activity of superoxide dismutase (SOD) reduced by blue light. Specifically, the samples increased the SOD activity, which had been reduced by 32.64% by blue light, by levels of 100.91% (Example 1) and 92.3% (Example 2), thereby effectively increasing the antioxidant activity.

As shown in FIG. 4 below, it was confirmed that the samples treated with the compounds (Examples 1 and 2) of the present invention significantly reduced the carbonylated protein increased by blue light. Specifically, the samples treated with the compounds (Examples 1 and 2) of the present invention significantly reduced the carbonylated protein, which had increased by 72.04% by blue light, by levels of 11.39% (Example 1) and 16.67% (Example 2), thereby inhibiting the cell damage and effectively protecting the skin.

According to the present invention, the cosmetic composition exerts a significant effect on protection of the skin by effectively inhibiting the generation of reactive oxygen species induced by the inner and outer changes of the skin or removing the reactive oxygen species; and inhibiting skin cell damage caused by ultraviolet rays or blue light. Also, the cosmetic composition increases the superoxide dismutase activity reduced by the reactive oxygen species, thereby protecting the skin.

According to the present invention, the cosmetic composition can inhibit expression levels of genes associated with the cell growth, and thus can be effective for protecting the skin and improving the skin conditions as well. Also, the cosmetic composition provides advantages in that it can exert a significant effect as a composition for protecting and improving the skin damaged by reactive oxygen species, ultraviolet rays, or blue light because it is safe for the human body, and causes no side effects even when used for a long period of time.

Hereinabove, although the present invention has been described with reference to the specific subject matters and limited embodiments thereof, they have been provided only for assisting in the entire understanding of the present invention. Therefore, the present invention is not limited to the exemplary embodiments. Various modifications and changes may be made from this description by those skilled in the art to which the present invention pertains.

Therefore, the spirit of the present invention should not be limited to the embodiments as described herein, and the following claims as well as all modifications equal or equivalent to the claims are intended to fall within the scope and spirit of the invention.

What is claimed is:

1. A cosmetic composition for protection of the skin against reactive oxygen species, ultraviolet rays, or blue light, comprising N-(2-hydroxyethyl)-2-methyl-hexanamide, N-(2-ethyl-1-oxohexyl)glycine methyl ester, or a combination thereof as an active ingredient.

2. The cosmetic composition of claim 1, wherein the cosmetic composition inhibits generation of reactive oxygen species or removes the reactive oxygen species.

3. The cosmetic composition of claim 2, wherein the reactive oxygen species are selected from hydrogen peroxide, a superoxide anion, and a hydroxy radical.

4. The cosmetic composition of claim 1, wherein the cosmetic composition inhibits generation of reactive oxygen species generated by ultraviolet rays or blue light or removes the reactive oxygen species to exhibit a skin protection activity.

5. The cosmetic composition of claim 1, wherein the cosmetic composition increases an activity of SOD.

6. The cosmetic composition of claim 1, wherein the cosmetic composition decreases expression of P16.

7. The cosmetic composition of claim 1, wherein the active ingredient is included at 0.001 to 5% by weight, based on the total weight of the cosmetic composition.

8. The cosmetic composition of claim 1, wherein the cosmetic composition is formulated into a lotion, a toner, a face lotion, an eye cream, a nourishing cream, a massage cream, a cleansing cream, a cleansing foam, a cleansing water, an essence, or a pack.

9. A method for improving skin conditions using, as a cosmetic material, a composition comprising N-(2-hydroxyethyl)-2-methyl-hexanamide, N-(2-ethyl-1-oxohexyl)glycine methyl ester, or a combination thereof as an active ingredient.

10. The method of claim 9, wherein the improvement is achieved by inhibiting generation of reactive oxygen species and removing the reactive oxygen species; increasing an activity of SOD; and decreasing expression of P16.

* * * * *